United States Patent

Monneret et al.

(10) Patent No.: US 6,281,198 B1
(45) Date of Patent: Aug. 28, 2001

(54) 9-(3,5-DIMETHOXYPHENYL)-5,8,8A,9-TETRAHYDROFURO-[3',4':6,7]NAPHTHO[2,3-D][1,3]DIOXOL-6(5AH)-ONE COMPOUNDS

(75) Inventors: Claude Monneret; Emmanuel Bertounesque, both of Paris; Philippe Meresse, Salesches; Ghanem Atassi, Saint-Cloud; Alain Pierre, Les Alluets le Roi; Bruno Pfeiffer, Saint leu la Foret; Pierre Renard, Le Chesnay, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/697,248

(22) Filed: Oct. 26, 2000

(30) Foreign Application Priority Data

Oct. 28, 1999 (FR) .................................................. 99 13514

(51) Int. Cl.$^7$ ........................ A61K 31/365; C07D 493/04
(52) U.S. Cl. ............................ 514/27; 514/463; 536/17.2; 536/18.1; 549/298
(58) Field of Search ................. 549/298; 514/463, 514/27; 536/17.2, 18.1

(56) References Cited

PUBLICATIONS

Mann et al, J. Chem. Soc., Chem. Commun., p. 430–432, 1982.*
Kuo et al, Heterocycles, vol. 36, No. 3, p.529–535, 1993.*
Kuhnt et al, Phytochemistry, vol. 36, No. 2, p. 485–489, 1994.*

\* cited by examiner

Primary Examiner—Bernard Dentz
(74) Attorney, Agent, or Firm—The Firm of Hueschen & Sage; G. Patrick Sage

(57) ABSTRACT

Compound of formula (I):

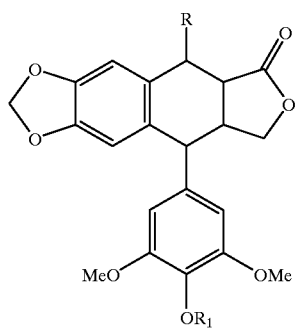

wherein:

R represents:

a group of formula (i):

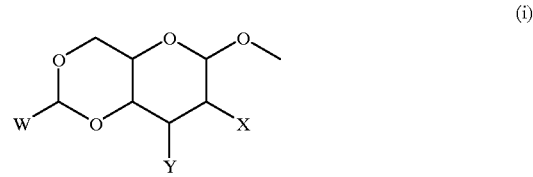

wherein X, Y and W are as defined in the description, or a group of formula (ii):

—A—G (ii)

wherein:

A represents a single bond or an optionally substituted alkylene chain,

G represents a group selected from hydrogen, cycloalkyl, heterocycloalkyl, aryl, heteroaryl, —$OR_2$, —O—$T_1$—$NR_3R_4$, —O—$T_1$—$NR_2$—$T'_1$—$NR_3R_4$, —$NR_3R_4$, —$NR_2$—$T_1$—$NR_3R_4$, —$NR_2$—$T_1$—$OR_5$, —$NR_2$—$T_1$—$CO_2R_6$, —$NR_2$—$T_1$—$C(O)R_6$, —$C(O)$—$NR_3R_4$, —$C(O)$—$NR_2$—$T_2$, —O—$C(O)T_2$, —O—$C(S)$—$T_2$, —$NR_2$—$C(O)$—$T_2$, —$NR_2$—$C(S)$—$T_2$, —O—$C(O)$—O—$T_2$, —O—$C(O)$—$NR_2$—$T_2$, —O—$C(S)$—O—$T_2$, —O—$C(S)$—$NR_2$—$T_2$, —$NR_2$—$C(O)$—O—$T_2$, —$NR_2$—$C(O)$—$NR$—$T_2$, —$NR_2$—$C(S)$—O—$T_2$, —$NR_2$—$C(S)$—$NR_6$—$T_2$ and —$NR_2$—$SO_2$—$T_3$, wherein $R_2$, $R_3$, $R_4$, $R_5$, $R_6$, $T_1$, $T'_1$, $T_2$ and $T_3$ are as defined in the description, $R_1$ represents a group selected from hydrogen, alkyl, aryl, arylalkyl, heteroaryl, heteroarylalkyl, alkylcarbonyl, arylcarbonyl, arylalkylcarbonyl, heterocycloalkylcarbonyl, alkylsulphonyl, arylsulphonyl, arylalkylsulphonyl, phosphono, aryloxycarbonyl, alkoxycarbonyl and arylalkoxycarbonyl, its isomers, and also addition salts thereof with a pharmaceutically acceptable acid or base.

Medicinal products containing the same which are useful in the treatment of cancer.

13 Claims, No Drawings

9-(3,5-DIMETHOXYPHENYL)-5,8,8A,9-TETRAHYDROFURO-[3',4':6,7]NAPHTHO[2,3-D][1,3]DIOXOL-6(5AH)-ONE COMPOUNDS

The present invention relates to new 9-(3,5-dimethoxyphenyl)-5,8,8a,9-tetrahydrofuro-[3',4':6,7]naphtho[2,3-d][1,3]dioxol-6(5aH)-one compounds.

BACKGROUND OF THE INVENTION

The compounds of the invention are derivatives of podophyllotoxin, a natural extract known for its use in the treatment of cancer. Other synthetic compounds, such as etoposide and teniposide, are currently used as chemotherapeutic agents in the treatment especially of small-cell lung cancer. Those various compounds act by inhibiting the catalytic activity of topoisomerase II.

DESCRIPTION OF THE PRIOR ART

Various modifications have been made to those compounds, such as the modifications described in the Patent Specifications JP 948 782, WO 97/13776 and U.S. Pat. No. 3,634,459.

Nevertheless, anti-cancer therapeutic requirements call for the constant development of new anti-tumour and cytotoxic agents with the aim of obtaining medicaments that are simultaneously more active, more soluble and better tolerated.

In addition to the fact that the compounds of the present invention are new, they have a surprising in vitro and in vivo activity that is superior to that observed hitherto. The compounds discovered by the Applicant accordingly have properties that render them particularly useful in the treatment of cancers.

DETAILED DESCRIPTION OF THE INVENTION

More especially, the present invention relates to the compounds of formula (I):

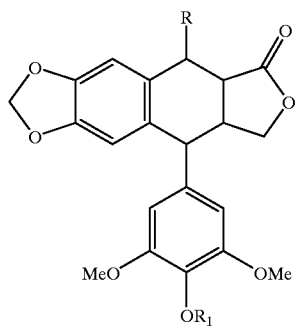

(I)

wherein:

R represents:

a group of formula (i):

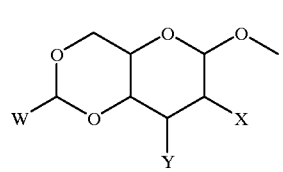

(i)

wherein:
X and Y, which may be identical or different, each represents a group selected from hydrogen, hydroxy, linear or branched $(C_1-C_6)$alkoxy, amino, linear or branched $(C_1-C_6)$alkylamino and di-$(C_1-C_6)$alkylamino in which each alkyl moiety may be linear or branched, W represents a hydrogen atom, a linear or branched $(C_1-C_6)$alkyl group, aryl or heteroaryl, or a group of formula (ii):

   (ii)

wherein:
A represents a single bond or a linear or branched $(C_1-C_6)$ alkylene chain optionally substituted by one or more identical or different groups selected from halogen and hydroxy and optionally containing an unsaturation, G represents a group selected from hydrogen, cycloalkyl, heterocycloalkyl, aryl, heteroaryl, $—OR_2$, $—O—T_1—NR_3R_4$, $—O—T_1—NR_2—T'_1—NR_3R_4$, $—NR_3R_4$, $—NR_2—T_1—NR_3R_4$, $—NR_2—T_1—OR_5$, $—NR_2—T_1—CO_2R_6$, $—NR_2—T_1—C(O)R_6$, $—C(O)NR_3R_4$, $—C(O)—NR_2—T_2$, $—O—C(O)—T_2$, $—O—C(S)—T_2$, $—NR_2—C(O)—T_2$, $—NR_2—C(S)—T_2$, $—O—C(O)—O—T_2$, $—O—C(O)—NR_2—T_2$, $—O—C(S)—O—T_2$, $—O—C(S)—NR_2—T_2$, $—NR_2—C(O)—O—T_2$, $—NR_2—C(O)—NR_6—T_2$, $—NR_2—C(S)—O—T_2$, $—NR_2—C(S)—NR_6—T_2$ and $—NR_2—SO_2—T_3$
wherein:
$R_2$ represents a hydrogen atom, a linear or branched $(C_1-C_6)$alkyl group, aryl or aryl-$(C_1-C_6)$alkyl in which the alkyl moiety may be linear or branched, $T_1$ and $T'_1$, which may be identical or different, each represents a linear or branched $(C_1-C_6)$alkylene chain, $R_3$ and $R_4$, which may be identical or different, each represents independently of the other:
a hydrogen atom, a linear or branched $(C_1-C_6)$alkyl group (optionally substituted by one or more hydroxy groups), aryl, aryl-$(C_1-C_6)$alkyl in which the alkyl moiety may be linear or branched, cycloalkyl, heteroaryl-$(C_1-C_6)$alkyl in which the alkyl moiety may be linear or branched, heteroaryl, heterocycloalkyl, or heterocycloalkyl-$(C_1-C_6)$alkyl in which the alkyl moiety may be linear or branched, or form together with the nitrogen atom carrying them a saturated or unsaturated, 5- to 7-membered, monocyclic heterocycle optionally containing a second hetero atom selected from oxygen and nitrogen, the said heterocycle being optionally substituted by one or more groups selected from halogen, hydroxy, linear or branched $(C_1-C_6)$alkyl and heterocyclic groups, $R_5$ represents a linear or branched $(C_1-C_6)$alkyl group, aryl or aryl-$(C_1-C_6)$alkyl in which the alkyl moiety may be linear or branched, $R_6$ represents a hydrogen atom, a linear or branched $(C_1-C_6)$alkyl group, aryl or aryl-$(C_1-C_6)$alkyl in which the alkyl moiety may be linear or branched, $T_2$ represents a group selected from hydrogen, linear or branched $(C_1-C_6)$alkyl (optionally substituted by one or more halogen atoms), aryl, aryl-$(C_1-C_6)$alkyl in which the alkyl moiety may be linear or branched, cycloalkyl, cycloalkyl-$(C_1-C_6)$alkyl in which the alkyl moiety may be linear or branched, heterocycloalkyl and heterocycloalkyl-$(C_1-C_6)$alkyl in which the alkyl moiety may be linear or branched, or $T_2$ represents a linear or branched $(C_1-C_6)$alkylene chain, the said chain being substituted by one or more identical or different groups selected from —$NR_3R_4$, —$OR_2$, —$CO_2R_6$, —$NR_2$-C(O)$R_6$, —$NR_2$—$CO_2R_6$, —C(O)$R_6$, —C(O)$NR_3R_4$, —$NR_2$—$T_1$—$NR_3R_4$, —$NR_2$—$T_1$—OR6 and —O—$T_1$—$NR_3R_4$ wherein $R_2$, $R_4$, $R_6$ and $T_1$ are as defined hereinbefore, $T_3$ represents a group selected from linear or branched $(C_1-C_{20})$alkyl (optionally substituted by one or more groups selected from halogen, —$OR_2$, —$NR_2R_6$, nitro, cyano and azide), aryl, aryl-$(C_1-C_6)$alkyl in which the alkyl moiety may be linear or branched, cycloalkyl, cycloalkyl-$(C_1-C_6)$alkyl in which the alkyl moiety may be linear or branched, heterocycloalkyl, heterocycloalkyl-$(C_1-C_6)$alkyl in which the alkyl moiety may be linear or branched, heteroaryl and heteroaryl-$(C_1-C_6)$alkyl in which the alkyl moiety may be linear or branched, $R_1$ represents a group selected from hydrogen, linear or branched $(C_1-C_6)$alkyl, aryl, aryl-$(C_1-C_6)$alkyl in which the alkyl moiety may be linear or branched, heteroaryl, to heteroaryl-$(C_1-C_6)$alkyl in which the alkyl moiety may be linear or branched, linear or branched $(C_1-C_6)$alkylcarbonyl, arylcarbonyl, aryl-$(C_1-C_6)$alkylcarbonyl in which the alkyl moiety may be linear or branched, heterocycloalkylcarbonyl, linear or branched $(C_1-C_6)$alkylsulphonyl, arylsulphonyl, aryl-$(C_1-C_6)$alkylsulphonyl in which the alkyl moiety may be linear or branched, phosphono, linear or branched $(C_1-C_6)$alkoxycarbonyl, aryloxycarbonyl and aryl-$(C_1-C_6)$alkoxycarbonyl in which the alkoxy moiety may be linear or branched, to their isomers, and also to addition salts thereof with a pharmaceutically acceptable acid or base,
wherein:

aryl denotes a phenyl, biphenyl, naphthyl, dihydronaphthyl, tetrahydronaphthyl, indenyl or indanyl group, each of those groups optionally having one or more identical or different substituents selected from halogen, hydroxy, linear or branched $(C_1-C_6)$alkyl, linear or branched $(C_1-C_6)$alkoxy, cyano, nitro, amino, linear or branched $(C_1-C_6)$alkylamino, di-$(C_1-C_6)$ alkylamino in which each alkyl moiety may be linear or branched, linear or branched $(C_1-C_6)$alkylsulphonyl, linear or branched $(C_1-C_6)$alkylsulphonylamino, carboxy, linear or branched $(C_1-C_6)$alkoxycarbonyl, aryloxycarbonyl, aryl-$(C_1-C_6)$alkoxycarbonyl in which the alkoxy moiety may be linear or branched, linear or branched $(C_1-C_6)$hydroxyalkyl, linear or branched $(C_1-C_6)$trihaloalkyl, methylenedioxy, ethylenedioxy, morpholinyl, piperidyl, piperazinyl, linear or branched $(C_1-C_6)$alkylcarbonyloxy and linear or branched $(C_1-C_6)$alkylcarbonyl, heteroaryl denotes an aromatic monocyclic group, an aromatic bicyclic group, or a bicyclic group in which one of the rings is aromatic and the other ring is partially hydrogenated, each of which groups has from 5 to 12 ring members and contains in the ring system one, two or three identical or different hetero atoms selected from oxygen, nitrogen and sulphur, it being possible for the said heteroaryl optionally to be substituted by the same substituents as those decribed in the case of the aryl group, cycloalkyl denotes a monocyclic or bicyclic group that is saturated or unsaturated, but not of aromatic character, that contains from 3 to 10 carbon atoms and is optionally substituted by one or more identical or different groups selected from halogen, linear or branched $(C_1-C_6)$alkyl, linear or branched $(C_1-C_6)$trihaloalkyl, hydroxy, linear or branched $(C_1-C_6)$hydroxyalkyl, amino, linear or branched $(C_1-C_6)$alkylamino, di-$(C_1-C_6)$-alkylamino in which each alkyl moiety may be linear or branched, piperidyl, piperazinyl and morpholinyl, heterocycloalkyl is to be understood as a cycloalkyl group as defined above containing one or two identical or different hetero atoms selected from oxygen, nitrogen and sulphur, the said heterocycloalkyl being optionally substituted by one or more substituents such as those described in the case of the cycloalkyl group, with the proviso that $R_1$ does not represent a methyl group when R represents a group —A—G in which A represents a single bond and G represents a hydrogen atom.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned, without implying any limitation, sodium hydroxide, potassium hydroxide, triethylamine, tert-butylamine, etc.

Preferred substituents $R_1$ according to the invention are the hydrogen atom and the groups linear or branched $(C_1-C_6)$alkyl, linear or branched $(C_1-C_6)$alkoxycarbonyl, aryloxycarbonyl and aryl-$(C_1-C_6)$alkoxycarbonyl in which the alkoxy moiety may be linear or branched.

Very advantageously, preferred compounds of the invention are those in which $R_1$ represents a hydrogen atom.

According to an advantageous embodiment of the invention, preferred compounds of the invention are those in which R represents a group of formula (i) wherein:

X represents an amino group, linear or branched $(C_1-C_6)$ alkylamino or di-$(C_1-C_6)$-alkylamino in which each alkyl moiety may be linear or branched, and Y represents a hydroxy group; or X and Y are identical and each represents a hydroxy group; or X represents a hydrogen atom and Y represents an amino group, linear or branched $(C_1-C_6)$-alkylamino or di-$(C_1-C_6)$ alkylamino in which each alkyl moiety may be linear or branched, and W represents a methyl or 2-thienyl group.

Preferably, preferred compounds of the invention are those in which R represents a group of formula (i) such as:

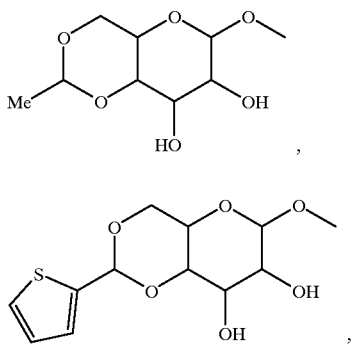

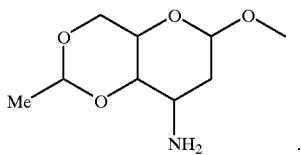

or

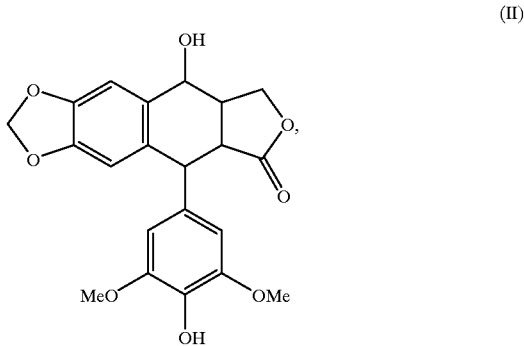

According to another especially advantageous embodiment of the invention, preferred compounds are those in which R represents a group of formula (ii) wherein:
A represents a single bond and
G represents a group selected from $O—T_1—NR_3R_4$, $—O—T_1—NR_2—T'_1—NR_3R_4$, $—NR_2—T_1—NR_3R_4$, $—NR_3R_4$, $—NR_2—T_1—OR_5$, $—O—C(O)—NR_2—T_2$ and $—NR_2—SO_2—T_3$ in which $T_1, T'_1, T_2, T_3, R_2, R_3, R_4$ and $R_5$ are as defined for formula (I).

Especially preferably, preferred compounds of the invention are those in which R represents a group of formula (ii) wherein:
A represents a single bond and
G represents a group $—O—C(O)—NR_2—T_2$ wherein $R_2$ and $T_2$ are as defined for formula (I) and, advantageously, $R_2$ represents a hydrogen atom or a linear or branched $(C_1-C_6)$alkyl group and $T_2$ represents an optionally substituted aryl group or a linear or branched $(C_1-C_6)$alkylene chain substituted by an $—NR_3R_4$ group wherein $R_3$ and $R_4$ are as defined for formula (I).

According to a third advantageous embodiment, preferred compounds of the invention are those in which R represents a group of formula (ii) wherein:
A represents a single bond and
G represents a group $—NR_2—SO_2—T_3$ wherein $R_2$ and $T_3$ are as defined for formula (I) and, advantageously, $R_2$ represents a hydrogen atom or a linear or branched $(C_1-C_6)$alkyl group and $T_3$ represents a linear or branched $(C_1-C_6)$alkyl group, aryl or heteroaryl.

Preferred compounds of the invention are:
9-(4-hydroxy-3,5-dimethoxyphenyl)-6-oxo-5,5a,6,8,8a,9-hexahydrofuro[3',4':6,7]naphtho[2,3-d][1,3]dioxol-5-yl 4-fluorophenylcarbamate,
9-(4-hydroxy-3,5-dimethoxyphenyl)-6-oxo-5,5a,6,8,8a,9-hexahydrofuro[3',4':6,7naphtho[2,3-d][1,3]dioxol-5-yl 2-(dimethylamino)ethyl(methyl)carbamate,
9-(4-hydroxy-3,5-dimethoxyphenyl)-6-oxo-5,5a,6,8,8a,9-hexahydrofuro[3',4':6,7]naphtho[2,3-d][1,3]-dioxol-5-yl 2-(dimethylamino)ethylcarbamate,
9-(4-hydroxy-3,5-dimethoxyphenyl)-6-oxo-5,5a,6,8,8a,9-hexahydrofuro[3',4':6,7]naphtho[2,3-d][1,3]dioxol-5-yl 3-(dimethylamino)propyl(methyl)carbamate,
and 9-(4-hydroxy-3,5-dimethoxyphenyl)-6-oxo-5,5a,6,8,8a,9-hexahydrofuro[3',4':6,7]naphtho[2,3-d][1,3]dioxol-5-yl 3-(dimethylamino)propylcarbamate.

The isomers and the addition salts with a pharmaceutically acceptable acid or base of the preferred compounds form an integral part of the invention.

Accordingly, the invention relates also to the respective isomers (5R,5aR,8aS,9R), (5R,5aS,8aR,9R), (5R,5aR,8aS,9R), (5R,5aR,8aS,9R) and (5R,5aS,8aR,9R) of the five above-listed compounds of formula (I).

The present invention extends also to a process for the preparation of the compounds of formula (I), which process is characterised in that there is used as starting material a compound of formula (II):

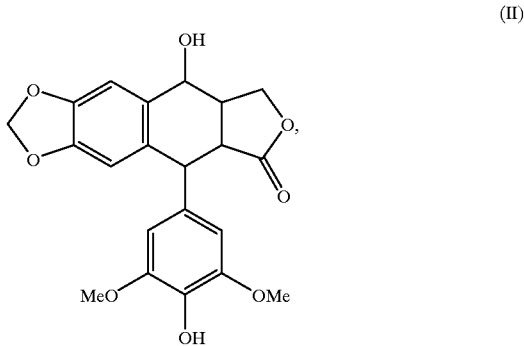

(II)

the hydroxy functions of which compoun of formula (II) are protected by a silyl protecting group conventionally used in organic chemistry, in accordance with the operating conditions customary in organic synthesis, to yield a compound of formula (III):

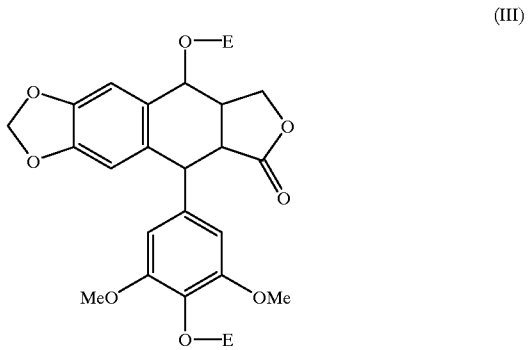

(III)

wherein E represasiylprotecting group,
which compound of formula (III) is treated with a reducing agent to yield a compound of formula (IV):

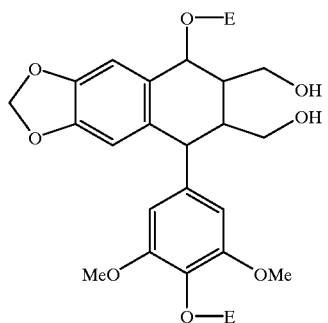

(IV)

wherein E is as defined hereinbefore,
which compound of formula (IV) is reacted in basic medium, in the presence of tetrapropylammonium perruthenate, to yield the compounds of formula (V):

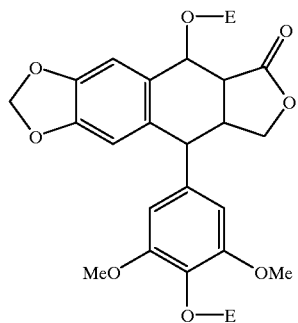

(V)

wherein E is as defined hereinbefore,
which compound of formula (V) is treated for several hours with tetrabutylammonium fluoride to yield the compounds of formula (I/a), a particular case of the compounds of formula (I):

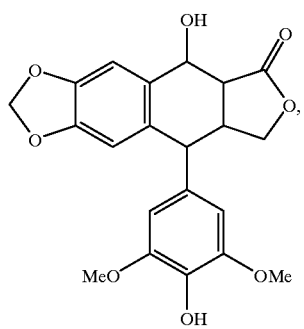

(I/a)

which compound of formula (I/a) is subjected, under basic conditions, to the action of a compound of formula (VII):

R'$_1$—X (VII)

wherein R'$_1$ represents a linear or branched (C$_1$–C$_6$)alkyl group, aryl, aryl-(C$_1$–C$_6$)alkyl in which the alkyl moiety may be linear or branched, heteroaryl, heteroaryl-(C$_1$–C$_6$)alkyl in which the alkyl moiety may be linear or branched, linear or branched (C$_1$–C$_6$)alkylcarbonyl, arylcarbonyl, aryl-(C$_1$–C$_6$)alkylcarbonyl in which the alkyl moiety may be linear or branched, heterocycloalkylcarbonyl, linear or branched (C$_1$–C$_6$) alkoxycarbonyl, aryloxycarbonyl, aryl-(C$_1$–C$_6$) alkoxycarbonyl in which the alkoxy moiety may be linear or branched, linear or branched (C$_1$–C$_6$) alkylsulphonyl, arylsulphonyl or aryl-(C$_1$–C$_6$) alkylsulphonyl in which the alkyl moiety may be linear or branched, and X represents a hydrogen atom or a halogen atom, to yield the compounds of formula (I/b), a particular case of the compounds of formula (I):

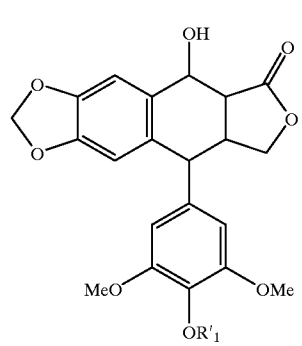

(I/b)

wherein R'$_1$ is as defined hereinbefore,
the totality of the compounds of formulae (I/a) and (I/b) constituting the compounds of formula (I/c):

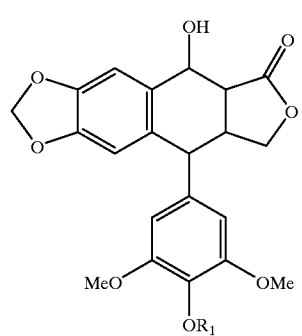

(I/c)

wherein R$_1$ is as defined for formula (I),
which compound of formula (I/c) is reacted:
with a compound of formula (VIII):

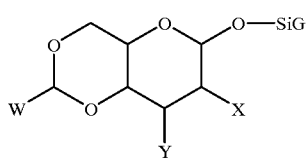

(VIII)

wherein X, Y et W are as defined for mula (I) and SiG represents a silyl protecting group conventionally used in sugar chemistry, in the presence of boron trifluoride etherate, to yield the compounds of formula (I/d), a particular case of the compounds of formula (I):

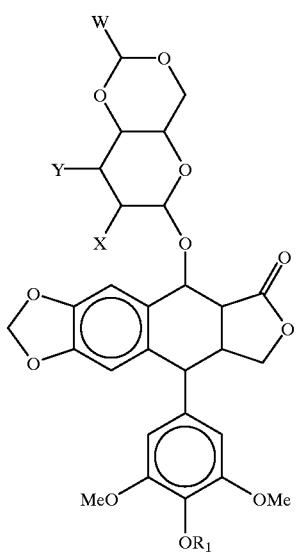

(I/d)

wherein X, Y, W and R$_1$ are as defined for formula (I), or, in the presence of a base, with a compound of formula (IX):

Hal—C(=M$_1$)—G$_2$ (IX)

wherein Hal represents a halogen atom, M$_1$ represents an oxygen or sulphur atom and G$_2$ represents a group T$_2$ or —O—T$_2$ wherein T$_2$ is as defined for formula (I), to yield the compounds of formula (I/e), a particular case of the compounds of formula (I):

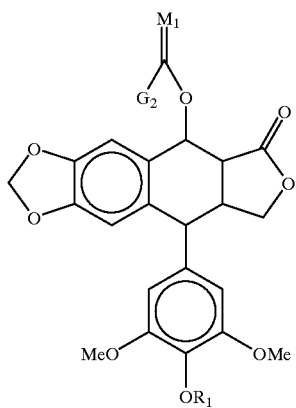

(I/e)

wherein R$_1$ is as defined for formula (I) and M$_1$ and G$_2$ are as defined hereinbefore,
or with a compound of formula (X):

M$_1$=C=N—T$_2$ (X)

wherein M$_1$ is as defined hereinbefore and T$_2$ is as defined for formula (I), to yield the compounds of formula (I/f), a particular case of the compounds of formula (I):

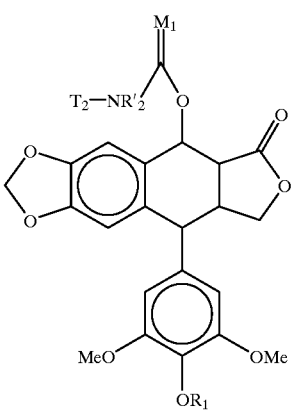

(I/f)

wherein R$_1$, M$_1$ and T$_2$ are as defined hereinbefore,
which compounds of formula (I/f) may be subjected to the action of a compound of formula (XI):

R'$_2$—Hal (XI)

wherein Hal represents a halogen atom and R'$_2$ has the same meanings as R$_2$ in formula (I): with the exception of a hydrogen atom,
to yield the compounds of formula (I/g), a particular case of the compounds of formula (I):

(I/g)

wherein R$_1$, R'$_2$, T$_2$ and M$_1$ are as defined hereinbefore,
or with sodium azide to yield the compounds of formula (XIa):

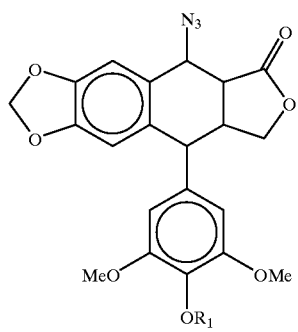

(XIa)

wherein $R_1$ is as defined hereinbefore, the azide function of which compounds of formula (XIa) is reduced to the primary amine function, and which compounds are then reacted:

with a compound of formula (X) as defined hereinbefore to yield the compounds of formula (I/h), a particular case of the compounds of formula (I):

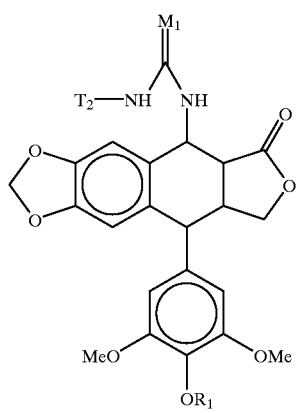

(I/h)

wherein $R_1$, $M_1$ and $T_2$ are as defined hereinbefore, the two nitrogen atoms of the urea or thiourea function of which compounds of formula (I/h) can readily be functionalised, in accordance with the conditions conventional in organic synthesis, by treatment in basic medium with a compound of formula (XI) $R'_2$—Hal as defined hereinbefore, to yield a monofunctionalised or difunctionalised urea or thiourea of formula —$NR_2$—$C(M_1)$—$NR_2$—$T_2$, or with a compound of formula (IX) as defined hereinbefore to yield the compounds of formula (I/i), a particular case of the compounds of formula (I):

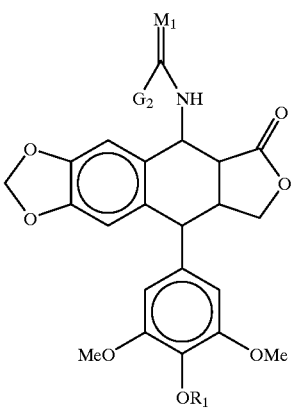

(I/i)

wherein $R_1$, $M_1$ and $G_2$ are as defined hereinbefore, the nitrogen atom of which compounds of formula (I/i) can readily be functionalised, in accordance with the conditions conventional in organic synthesis, by treatment in basic medium with a compound of formula (XI) as defined hereinbefore, or with a compound of formula (XII):

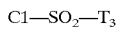

$$Cl—SO_2—T_3 \qquad (XII)$$

wherein $T_3$ has the same definition as for formula (I) to yield the compounds of formula (I/j), a particular case of the compounds of formula (I):

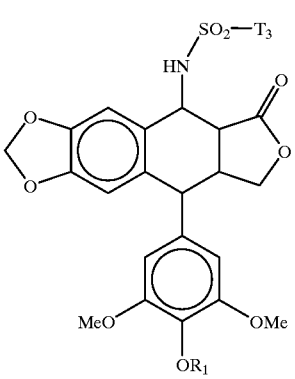

(I/j)

wherein $R_1$ and $T_3$ are as defined hereinbefore, or with a compound of formula (XIII):

$$Hal—G_3 \qquad (XIII)$$

wherein Hal represents a halogen atom and $G_3$ represents a group selected from —$R'_2$, —$T_1$—$NR_3R_4$ and —$T_1$—$NR_2$—$T'_1$—$NR_3R_4$ wherein $R'_2$, $R_2$, $R_3$, $R_4$, $T_1$ and $T'_1$ are as defined hereinbefore, to yield the compounds of formula (I/k), a particular case of the compounds of formula (I):

(I/k)

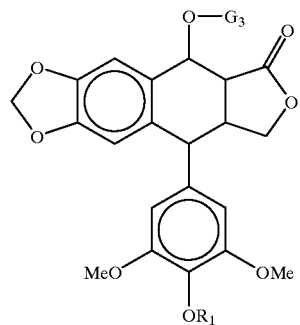

wherein $R_1$ and $G_3$ are as defined herein before, or with gaseous hydrogen chloride or hydrogen bromide to yield the compounds of formula (XIV):

(XIV)

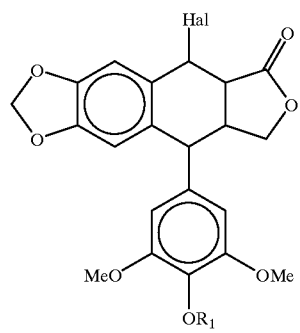

wherein Hal represents a chlorine or bromine atom and $R_1$ is as defined for formula (I), which compounds of formula (XIV) are treated in basic medium with a compound of formula (XV) or of formula (XVbis):

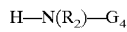 (XV)

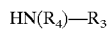 (XVbis), in which formulae $R_2$, $R_3$ and $R_4$ are as defined for formula (I) and $G_4$ represents a group of formula $-T_1-NR_3R_4$, $-T_1-OR_5$, $-T_1-CO_2R_6$ or $T_1-CO-R_6$ wherein $T_1$, $R_3$, $R_4$, $R_5$ and $R_6$ have the same meanings as for formula (I), to yield the compounds of formula (I/l) and (I/m), a particular case of the compounds of formula (I), (I/l)

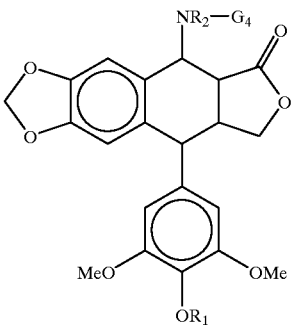

(I/m)

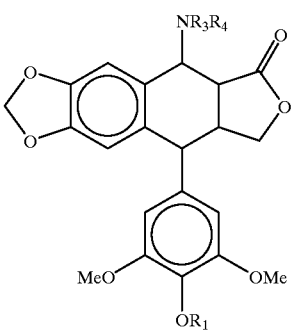

wherein $R_1$, $R_2$, $R_3$, $R_4$ and $G_4$ are as defined hereinbefore, or is reacted, in the presence of boron trifluoride etherate, with a compound of formula (XVI):

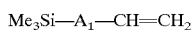 (XVI):

wherein $A_1$ represents a linear or branched ($C_1$-$C_5$) alkylene chain to yield the compounds of formula (I/n), a particular case of the compounds of formula (I):

(I/n)

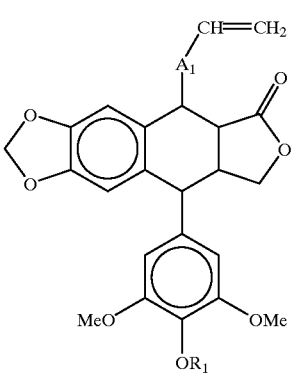

wherein $R_1$ and $A_1$ are as defined hereinbefore:
which compounds of formula (I/n) are treated with osmium tetroxide in the presence of N-methylmorpholine oxide and then oxidised by the action of lead tetraacetate to yield the compounds of formula (XVII):

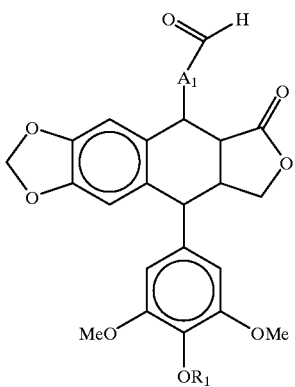

(XVII)

wherein A₁ and R₁ are as defined hereinbefore,
which compounds of formula (XVII) are then easily treated, by conventional methods of reduction, oxidation or electrophilic or nucleophilic addition that are well known to the person skilled in the art of organic synthesis, to yield the compounds of formula (I/o), a particular case of the compounds of formula (I):

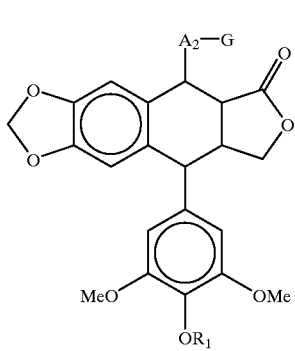

(I/o)

wherein R₁ is as defined hereinbefore, G has the same definition as for formula (I) and A₂ has the same meanings as A in formula (I) with the exception of the definition single bond, the compounds (I/a) to (I/o) constituting the totality of the compounds of formula (I) of the invention, which compounds are purified, if necessary, according to a conventional purification technique, may be separated, if desired, into their different isomers according to a conventional separation technique, and are optionally converted into their addition salts with a pharmaceutically acceptable acid or base.

The compounds of formulae (XIa), (XIV) and (XVII) are useful as synthesis intermediates for the preparation of the compounds of formula (I).

The compounds of formulae (II), (VII), (VIII), (IX), (X), (XI), (XII), (XIII), (XV), (XVbis) and (XVI) are either commercially available compounds, or are obtained according to conventional methods of organic synthesis.

The compounds of formula (I) exhibit especially valuable anti-tumour properties. They have an excellent cytotoxicity in vitro on cell lines from murine and human tumours and are active in vivo. The characteristic properties of these compounds enables them to be used therapeutically as anti-tumour agents.

The present invention relates also to pharmaceutical compositions comprising as active ingredient at least one compound of formula (I), an optical isomer thereof or an addition salt thereof with a pharmaceutically acceptable acid or base, alone or in combination with one or more pharmaceutically acceptable, inert, non-toxic excipients or carriers.

Among the compositions according to the invention there may be mentioned more especially those which are suitable for oral, parenteral (intravenous, intramuscular or subcutaneous) per- or trans-cutaneous, nasal, rectal, perlingual, ocular or respiratory administration, and especially tablets or dragees, sublingual tablets, soft gelatin capsules, hard gelatin capsules, suppositories, creams, ointments, dermal gels, injectable or drinkable preparations, aerosols, eye or nose drops, etc.

The useful dosage varies in accordance with the the age and weight of the patient, the administration route, the nature and severity of the disorder and the administration of possible associated treatements and ranges from 0.5 to 500 mg per day taken in one or more administrations.

The following Examples illustrate the invention but do not limit it in any way. The starting materials employed are either known products or are products prepared according to known procedures.

The structures of the compounds described in the Examples were determined according to customary spetrophotometric techniques (infra-red, nuclear magnetic resonance, mass spectrometry . . . ).

EXAMPLE 1

(5R,5aR,8aS,9R)-5-hydroxy-9-4-hydroxy-3,5-dimethoxyphenyl)-5,8,8a,9-tetrahydrofuro[3',4':6,7] naphtho[2,3-d][1,3]dioxol-6-one

STEP A:

(5R,5aS,8aS,9R)-9-{[tert-butyl(dimethyl)silyl]oxy}-5-(4-{[tert-butyl-(dimethyl)silyl]oxy}-3,5-dimethoxyphenyl)-5,8,8a,9-tetrahydrofuro-3',4':6,7] naphtho[2,3-d][1,3]dioxo-6-one 54.4 mmol of tert-butyldimethylsilyl triflate are added dropwise, at 0° C. and under an inert atmosphere, to a solution of 13.6 mmol of 4'-demethylepipodophyllotoxin and 81.7 mmol of 2,6-lutidine in 200 ml of anhydrous dichloromethane. After stirring the reaction mixture for 1 hour 30 minutes at 0° C., 200 ml of water are added thereto. The organic phase is then washed until neutral, dried, filtered and concentrated under reduced pressure. Chromatography on silica gel (cyclohexane/ethyl acetate: 95/5) enables the expected product to be isolated.

Melting point 172–173° C.

STEP B:

[(5R,6S,7S,8R)-5{[tert-butyl(dimethyl)silyl]oxy}-8-(4-{[tert-butyl-(dimethy)siyl]oxy}-3,5-dimethoxyphenyl)-7-(hydroxymethyl)-5,6,7,8-tetrahydronaphtho[2,3-d][1,3]dioxo-6-yl]methanol 16 mmol of lithium aluminium hydride are added to a solution of 10.6 mmol of the compound of Step A in 200 ml of anhydrous tetrahydrofuran that has been placed at 0° C. under argon. After 15 minutes' stirring at 0° C. and then at ambient temperature, 0.6 ml of water, 0.6 ml of an aqueous 15% sodium hydroxide solution and then 1.8 ml of water are added in succession to the reaction mixture, bringing about the formation of a precipitate. After removal of the precipitate by filtration, the filtrate is concentrated under reduced pressure. Chromatography on silica gel (cyclohexane/ethyl acetate: 3/1) enables the expected product to be isolated.

Melting point: 156–158° C.

STEP C:

(5R,5aR,8aS,9R)-5-{[tert-butyl(dimethyl)silyl]oxy}-
9-(4-{[tert-butyl-(dimethyl)silyl]oxy}-3,5-
dimethoxyphenyl)5,8,8a,9-tetrahydrofuro-[3',4':6,7]
naphtho[2,3-d][1,3]dioxol-6(5aH)-one 1.97 g of 4Å molecular sieve, 11.8 mmol of 4-methylmorpholine N-oxide and then 0.4 mmol of tetrapropylammonium perruthenate are added to a solution of 3.95 mmol of the compound of Step B in 80 ml of anhydrous dichloromethane. After 2 hours at ambient temperature, the reaction mixture is filtered over Celite and then concentrated under reduced pressure. Chromatography on silica gel (cyclohexane/ethyl acetate: 96/4 then 95/5) enables the isolation of a 1:1 mixture consisting of the expected product and the product obtained in Step A.

Melting point: 193–494° C.

STEP D:

(5R,5aR,8aS,9R)-5-{[tert-butyl(dimethyl)silyl]oxy}-
9-(4-hydroxy-3,5-dimethoxyphenyl)-5,8,8a,9-
tetrahydrofuro[3',4':6,7]naphtho[2,3d-][1,3]-dioxol-6
(5aH)-one 4.3 mmol of a 1M solution of tetrabutylammonium fluoride in tetrahydrofuran are added dropwise, under argon, to a solution of 2.78 mmol of the mixture obtained in Step C in 60 ml of anhydrous tetrahydrofuran. After 20 minutes' reaction, 35 ml of a saturated aqueous ammonium chloride solution, 50 ml of water and then 100 ml of ethyl acetate are added to the reaction mixture. After extraction with ethyl acetate, the organic phases are washed, dried, filtered and then concentrated under reduced pressure. Chromatography on silica gel (cyclohexane/ethyl acetate) enables the expected product to be isolated.

Mass spectrum (DIC/NH$_3$): m/z=532 [M+NH$_4$]$^+$

STEP E:

(5R,5aR,8aS,9R)-5-hydroxy-9-(4-hydroxy-3,5-
dimethoxyphenyl)-5,8,8a,9-tetrahydrofuro[3',4':6,7]
naphtho[2,3-d][1,3]dioxol-6-one The procedure is as in the above Step D, using as substrate the product obtained in Step D and continuing the reaction, with stirring, for 23 hours.

Melting point 129–131° C.; Mass spectrum (DIC/NH$_3$): m/z=418 [M+NH$_4$]$^+$.

EXAMPLE 2

4-[(5R,5aS,8aR,9R)9-hydroxy-8-oxo-5,5a,6,8,8a,9-
hexahydrofuro-[3',4':6,7]naphtho[2,3-d][1,3]-dioxol-
5yl]-2,6dimethoxyphenyl benzyl carbonate 0.55 mmol of triethylamine and 0.37 mmol of benzyl chloroformate are added in succession, at 0° C. and under argon, to a solution of 0.25 mmol of the compound of Example 1 in 10 ml of anhydrous dichloromethane. After stirring for 1 hour, the reaction mixture is washed with water. The organic phase is then dried, filtered and subsequently concentrated under reduced pressure. Chromatography on silica gel (cyclohexane/ethyl acetate: 60/40) enables the expected product to be isolated.

Meltine point: 128–130° C.; High-resolution mass spectrum (DIC/NH$_3$): m/z (measured)=552.1870 [NH$_4$$^+$; m/z (calculated)=552.1866 [M+NH$_4$]$^+$.

EXAMPLE 3

4-((5R,5aS,8aR,9R)-9-{[(4-fluoroanilino)carbonyl]
oxy}-8-oxo-5,5a,6,8,8a,9-hexahydrofuro[3',4':6,7]
naphtho[2,3-d][1,3]-dioxol-5-yl)2,6-
dimethoxyphenyl benzyl carbonate To a solution, under argon, of 0.19 mmol of the compound of Example 2 in 10 ml of anhydrous dichloromethane there are added 0.038 mmol of 4-dimethylaminopyridine and 0.38 mmol of 2,6-lutidine and then, dropwise, 0.27 mmol of 4-fluorophenyl isocyanate. After reaction of the reaction mixture for 22 hours, 0.15 mmol of 2,6-lutidine and 0.095 mmol of 4-fluorophenyl isocyanate are added thereto. After reaction for 21 hours, the reaction mixture is hydrolysed and the organic phase is washed, dried, filtered and then concentrated under reduced pressure. Chromatography on silica gel (cyclohexane/ethyl acetate: 3/1) enables the expected product to be isolated.

Melting point: 202–204° C.; Mass spectrum (DIC/NH$_3$): m/z=689 [M+NH$_4$]$^+$.

EXAMPLE 4

(5R,5aR,8aS,9R)-9-(4-hydroxy-3,5-
dimethoxyphenyl)-6-oxo-5,5a,6,8,8a,9-
hexahydrofuro[3',4':6,7]naphtho[2,3-d][1,3]dioxol-5-
yl 4-fluorophenylcarbamate 50 mg of 5% Pd/C are added to a solution of 0.1 mmol of the compound of Example 3 in 8 ml of ethyl acetate. The reaction mixture is placed under a hydrogen atmosphere at atmospheric pressure. After stirring the mixture for 1 hour, the catalyst is filtered off over Celite and the filtrate is concentrated under reduced pressure. Chromatography on silica gel (cyclohexane/ethyl acetate: 2/1) enables the expected product to be isolated.

Melting point: 171–176° C.; Mass spectrum (DIC/NH$_3$): m/z=555 [M+NH$_4$]$^+$.

EXAMPLE 5

(5R,5aR,8aS,9R)-9-(4-{[(benzyloxy)carbonyl]oxy}-
3,5-dimethoxyphenyl-6-oxo-5,5a,6,8,8a,9-
hexahydrofuro[3',4':6,7]naphtho[2,3-d][1,3]dioxol-5-
yl 4-nitrophenylcarbonate 3.61 mmol of pyridine and then, dropwise, 0.95 mmol of the compound of Example 3 diluted with 10 ml of dichloromethane, are added to a solution of 3.23 mmol of 4-nitrophenyl chloroformate in 30 ml of anhydrous dichloromethane under argon. After 1 hour 15 minutes at ambient temperature, the reaction mixture is hydrolysed. After extraction with dichloromethane, the organic phases are washed, dried, filtered and then concentrated under reduced pressure. Chromatography on silica gel (cyclohexane/ethyl acetate: 3/1) enables the expected product to be isolated.

Melting point: 125–13° C.; Mass spectrum (FAB$^+$): m/z= 698 [M−H]$^+$.

EXAMPLE 6

4-[(5R,5aS,8aR,9R)-9-({[[2-dimethylamino)ethyl]
(methyl)amino]carbonyl}oxy)-8-oxo-5,5a,6,8,8a,9-
hexahydrofuro[3',4':6,7]naphtho[2,3-d][1,3]dioxol-5-
yl]-2,6-dimethoxyphenyl benzyl carbonate 0.225 mmol of N,N,N'-trimethylethylenediamine and 0.225 mmol of triethylamine are added in succession to a solution of 0.15 mmol of the compound of Example 5 in 3 ml of anhydrous dichloromethane. After stirring for 1 hour 30 minutes, the reaction mixture is hydrolysed. The organic phase is then washed, dried, filtered and subsequently concentrated under reduced pressure. Chromatography on silica gel (dichloromethane/methanol 96/4) enables the expected product to be isolated.

Melting point: 102–104° C.; Mass spectrum (DIC/NH$_3$): m/z=663 [M+H]$^+$.

EXAMPLE 7

(5R,5aR,8aS,9R)-9-(4-hydroxy-3,5-dimethoxyphenyl)-6-oxo-5,5a,6,8,8a,9-hexahydrofuro[3',4':6,7]naphtho[2,3-d][1,3]dioxol-5-yl 2-(dimethylamino)ethyl(methyl)carbamate The compound of Example 6 is subjected to the same operating conditions as those described in Example 4, enabling the expected product to be obtained.

Melting point: 133–135° C.; High-resolution mass spectrum (FAB$^+$): m/z (measured)=529.2180 [M+H]$^+$; m/z (calculaled)=529.2186 [M+H]$^+$.

EXAMPLE 8

4-{(5R,5aS,8aR,9R)-9-[({[2-(dimethylamino)ethyl]amino}carbonyl)oxyl-8-oxo-5,5a,6,8,8a,9-hexahydrofuro[3',4':6,7]naphtho[2,3-d][1,3]dioxol-5-yl}-2,6-dimethoxyphenyl benzyl carbonate The product is obtained in accordance with the operating conditions described in Example 6, using as substrate the product of Example 5 and as reagent N,N-dimethylethylenediamine.

Melting point: 113–116° C.; High-resolution mass spectrum (FAB$^+$): m/z (measured)=649.2388 [M+H]$^+$; m/z (calculated)=649.2397 [(M+H]$^+$.

EXAMPLE 9

(5R,5aR,8aS,9R)-9-(4-hydroxy-3,5-dimethoxyphenyl)-6-oxo-5,5a,6,8,8a,9-hexahydrofuro[3',4':6,7]naphtho[2,3-d][1,3]dioxol-5-yl2-(dimethylamino)ethylcarbamate The product is obtained in accordance with the operating conditions described in Example 4, using as substrate the compound of Example 8.

Melting point: 140–142° C.; High-resolution mass spectrum (FAB$^+$): m/z (measured)=515.2043 [M+H]$^+$; m/z (calculated)=515.2030 [M+H]$^+$.

EXAMPLE 10

4-[(5R,5aS,8aR,9R)-9-({[[3-(dimethylamino)propyl](methyl)amino]-carbonyl}oxy)-8-oxo-5,5a,6,8,8a,9-hexahydrofuro[3',4':6,7]naphtho-12,3-d][1,3]dioxol-5-yl]-2,6-dimethoxyphenyl benzyl carbonate The product is obtained in accordance with the operating conditions described in Example 6, using as substrate the product of Example 5 and as reagent N,N,N'-trimethyl1,3-propanediamine.

Melting point: 124–126° C.; High-resolution mass spectrum (FAB$^+$): m/z (measured)=677.2725 [M+NH$_4$]$^+$; m/z (calculated)=677.2710 [M+NH$_4$]$^+$.

EXAMPLE 11

(5R,5aR,8aS,9R)-9-(4-hydroxy-3,5-dimethoxyphenyl)-6-oxo-5,5a,6,8,8a,9-hexahydrofuro[3',4':6,7]naphtho[2,3-d][1,3]dioxol-5-yl3-(dimethylamino)propyl(methyl)carbamate The product is obtained in accordance with the operating conditions described in Example 4, using as substrate the compound of Example 10.

High-resolution mass spectrum (FAB$^+$): m/z (measured)=542.5781 [M+NH$_4$]$^+$; m/z (calculated)=542.5776 [M+NH$_4$]$^+$.

EXAMPLE 12

4-{(5R,5aS,8aR,9R)-9-[({[3-(dimethylamino)propyl]amino}-carbonyl)oxy]-8-oxo-5,5a,6,8,8a,9-hexahydrofuro[3',4':6,7]naphtho[2,3-d][1,3]dioxol-5-yl)-2,6-dimethoxyphenyl benzyl carbonate The product is obtained in accordance with the operating conditions described in Example 6, using as substrate the product of Example 5 and as reagent N,N-dimethyl-1,3-propanediamine.

Melting point: 102–104° C.; High-resolution mass spectrum (FAB$^+$): m/z (measured)=663.2539 [M+H]$^+$; m/z (calculated)=663.2554 [M+H]$^+$.

EXAMPLE 13

(5R,5aR,8aS,9R)-9-(4-hydroxy-3,5-dimethoxyphenyl)-6-oxo-5,5a,6,8,8a,9-hexahydrofuro[3',4':6,7]naphtho[2,3-d][2,3]dioxol-5-yl3-dimethylamino)propylcarbamate The product is obtained in accordance with the operating conditions described in Example 4, using as substrate the compound of Example 12.

High-resolution mass spectrum (FAB$^+$): m/z (measured)= 529.2180 [M+H]$^+$; mz (calculated)=529.2186 [M+H]$^+$.

EXAMPLE 14

(5S,5aR,8aS,9R)-5-amino-9-(4-hydroxy-3,5-dimethoxyphenyl)-5,8,8a,9-tetrahydrofuro[3',4':6,7]naphtho[2,3-d][1,3]dioxol-6(5aH)-one

STEP 1:

(5S,5aR,8aS,9R)-5-azido-9-(4-hydroxy-3,5-dimethoxyphenyl)-5,8,8a,9-tetrahydrofuro[3',4':6,7]naphtho[2,3-d][1,3]dioxol-6(5aH)-one 10.4 mmol of trifluoroacetic acid are added dropwise to a solution of 8 mmol of the compound of Example 1 and 40 mmol of sodium azide in 16 ml of chloroform. After stirring the reaction mixture for 15 minutes, a saturated aqueous sodium bicarbonate solution is added thereto. The organic phase is washed with water, dried, filtered and then concentrated under reduced pressure. Chromatography on silica gel (dichloromethane/ethyl acetate: 92/8) enables the expected product to be isolated.

STEP 2:

(5S,5aR,8aS,9R)-5-amino-9-(4-hydroxy-3,5-dimethoxyphenyl)-5,8,8a,9-tetrahydrofuro[3',4':6,7]naphtho[2,3-d][1,3]dioxol-6(5aH)-one 0.6 g of 10% Pd/C is added to a solution of 7 mmol of the compound obtained in Step 1 in 160 ml of ethyl acetate. The reaction mixture is then stirred under hydrogen for 16 hours and subsequently filtered over Celite. After concentration of the fil trate under reduced pressure, the residue is chromatographed on silica gel (dichloromethane/ethyl acetate: 90/10), enabling the expected product to be isolated.

EXAMPLE 15

4-{(5R,5aS,8aR,9S)-9-[(4-fluorobenzoyl)amino]-8-oxo-5,5a,6,8,8a,9-hexahydrofuro [3',4':6,7]naphtho [2,3-d][1,3]dioxol-5-yl}2,6-dimethoxyphenyl4-fluorobenzoate 1.65 mmol of triethylamine and then 1.70 mmol of para-fluorobenzoic acid chloride are added to a solution of 0.75 mmol of the compound obtained in Example 14 in 12 ml of anhydrous tetrahydrofuran. After stirring for 2 hours, the reaction mixture is evaporated. The residue is taken up in dichloromethane and water. After decanting off and extraction with dichloromethane, the organic phase is dried, filtered and then concentrated under reduced pressure. Chromatography on silica gel (dichloromethane/ac6tone: 95/5) enables the expected product to be isolated.

EXAMPLE 16

N-[(5S,5aR,8aS,9R)-9-(4-hydroxy-3,5-dimethoxyphenyl)-6-oxo-5,5a,6,8,8a,9-hexahydrofuro[3',4':6,7]naphtho[2,3-d][1,3dioxol-5-yl]-4-nitrobenzamide

STEP 1:

(5S,5aR,8aS,9R)-5-amino-9-[4-{[tert-butyl(dimethyl)silyl]oxy}-3,5-dimethoxyphenyl]-5,8,8a,9-tetrahydrofuro[3',4':6,7]naphtho[2,3-d][1,3]dioxol-6(5aH)-one A solution of 7.4 mmol of the compound of Example 14, 58.8 mmol of imidazole and 13 mmol of tert-butyldimethylsilyl chloride in 225 ml of anhydrous dimethylformarnide is stirred at ambient temperature. After reaction for 17 hours, the mixture is poured into a mixture of water and ether. After exraction with ether, the combined organic phases are dried, filtered and then concentrated under reduced pressure. The residue is subsequently recrystallised from a heptane/benzene mixture enabling the expected product to be isolated.

STEP 2:

N-[(5S,5aR,8aS,9R)-9-(4-hydroxy-3,5-dimethoxyphenyl)-6-oxo-5,5a,6,8,8a,9-hexahydrofuro[3',4':6,7]naphtho[2,3-d][1,3]dioxol-5-yl]-4-nitrobenzamide 0.4 mmol of 1,4-diazabicyclo[2.2.2]octane and then 0.78 mmol of para-nitrobenzoic acid are added to a solution of 0.6 mmol of the compound obtained in Step 1 in 10 ml of anhydrous dichloromethane. After 7 hours at ambient temperature, the reaction mixture is evaporated and the residue is chromatographed. The isolated product is then dissolved in 50 ml of methanol and Dowex 50X2-200 resin is added. After stirring for 15 hours at ambient temperature, the reaction mixture is filtered and then concentrated under reduced pressure, enabling the expected product to be isolated.

EXAMPLE 17

4-{(5R,5aS,8aR,9S)-9-[(methylsulphonyl)amino]-8-oxo-5,5a,6,8,8a,9-hexahydrofuro[3',4':6,7]naphtho[2,3-d][1,3]-dioxol-5-yl}-2,6-dimethoxyphenyl methanesulphonate The procedure is as in Example 15, using methanesulphonic acid chloride as the reagent.

EXAMPLE 18

N-[(5S,5aR,8aS,9R)-9-(4-hydroxy-3,5-dimethoxyphenyl)-6-oxo-5,5a,6,8,8a,9-hexahydrofuro[3',4':6,7]naphtho[2,3-d][1,3]-dioxol-5-yl)}4-(methylsulphonyl)benzenesulphonamide The procedure is as in Example 16, using 4-methanesulphonylbenzenesulphonic acid chloride as the reagent.

EXAMPLE 19

N-[(5S,5aR,8aS,9R)-9-(4-hydroxy-3,5-dimethoxyphenyl)-6oxo-5,5a,6,8,8a,9-hexahydrofuro[3',4':6,7]naphtho[2,3-d][1,3]-dioxol-5-yl]-2-thiophenesulphonamide The procedure is as in Example 16, using 2-thiophenesulphonic acid chloride as the reagent.

EXAMPLE 20

(5S,5aR,8aS,9R)-9-(4-hydroxy-3,5-dimethoxyphenyl)-5-propyl-5,8,8a,9-tetrahydrofuro[3',4':6,7]naphtho[2,3-d][1,3]-dioxol-6(5aH)-one

STEP 1:

4-[(5R,5aS,8aS,9S)-8-oxo-9-propenyl-5,5a,6,8,8a,9-hexahydrofuro[3',4':6,7]naphtho[2,3 d][1,3]-dioxol-5-yl]-2,6-dimethoxyphenyl benzyl carbonate 32.6 mmol of trimethylallylsilane and then 21.5 mmol of boron trifluoride etherate are added to a solution of 7.95 mmol of the compound of Example 2 in 80 ml of anhydrous dichloromethane. After stirring the reaction mixture for 2 hours at 0° C. and then for 30 minutes at ambient temperature, 32.7 mmol of pyridine are added thereto. After treating with dilute hydrochloric acid and then washing with water, the organic phase is decanted off and then the aqueous phase is extracted with dichloromethane. The combined organic phases are dried, filtered and then concentrated under reduced pressure. Chromatography on silica gel (dichloromethane/acetone: 96/4) enables the expected product to be isolated.

STEP 2:

(5S,5aR,8aS,9R)-9-(4-hydroxy-3,5-dimethoxyphenyl)-5-propyl-5,8,8a,9-tetrahydrofuro[3',4':6,7]naphtho[2,3-d][1,3]-dioxol-6(5aH)-one The procedure is as in Example 4, using as the substrate the product obtained in Step 1 above.

EXAMPLE 21

(5R,5aS,8aS,9R)-5-(2,3-dihydroxypropyl)-9-(4-hydroxy-3,5-dimethoxyphenyl)-5,8,8a,9-tetrahydrofuro[3',4':6,7]naphtho[2,3-d][1,3]dioxol-6(5aH)-one

STEP 1:

4-[(5R,5aS,8aS,9R)-9-(2,3-dihydroxypropyl)-8-oxo-5,5a,6,8,8a,9-hexahydrofuro]3',4':6,7]naphtho[2,3-d][1,3]dioxol-5-yl]-2,6-dimethoxyphenyl benzyl carbonate 0.17 mmol of osmium tetroxide is added to a solution of 1.92 mmol of the compound obtained in Step 1 of Example 20 and of 1.92 mmol of N-methylmorpholine oxide in 15 ml of anhydrous acetone. After stirring the reaction mixture for 2 hours at ambient temperature, a mixture of ice and a saturated aqueous sodium bisulfite solution is poured into the reaction mixture. After stirring for one hour, the mixture is extracted with dichloromethane. The organic phase is washed with 1N hydrochloric acid and subsequently with water, and then dried, filtered and concentrated under reduced pressure, enabling the expected product to be isolated.

STEP 2:

(5R,5aS,8aS,9R)-5-(2,3-dihydroxypropyl)-9-(4-hydroxy-3,5-dimethoxyphenyl)-5,8,8a,9-tetrahydrofuro[3',4':6,7]naphtho[2,3-d][1,3]dioxol-6(5aR)-one The procedure is as in Example 4, using as substrate the product obtained in Step 1 above.

EXAMPLE 22

(5R,5aR,8aS,9R)-5-{[(2S,6R,8R)-8-amino-2-methylhexahydropyrano[3,2-d][1,3]-dioxin-6-yl]oxy}-9-(4-hydroxy-3,5-dimethoxy-phenyl)-5,8,8a,9-tetrahydrofuro[3',4':6,7]naphtho[2,3-d][1,3]dioxol-6(5aH)one

STEP 1:

4-(5R,5aS,8aR,9R)-9-{[(2S,6R,8R)-8-azido-2-methylhexahydropyrano[3,2-d][1,3]dioxin-6-yl]oxy}-8-oxo-5,5a,6,8,8a,9-hexahydrofuro[3',4':6,7]naphtho[2,3-d][1,3]dioxol-5-yl)2,6-dimethoxyphenyl benzyl carbonate 2 g of 4 Å molecular sieve in powder form and 2.8 mmol of trimethylsilyl trifluoromethanesulphonate are added to a solution, cooled to −35° C., of 1.64 mmol of the compound of Example 2 and 1.64 mmol of (tert-butyl-dimethylsilyl)-3-azido-2,3-dideoxy-4,6—O—ethylidene-β-D-ribo-hexapyranoside in 20 ml of anhydrous dichloromethane. After 12 hours, the reaction mixture is diluted with dichloromethane, and then washed with a citrate buffer, pH 5, and water. After extraction, the organic phases are dried, filtered and then concentrated under reduced pressure. Chromatography on silica gel (cyclohexane/ethyl acetate: 2/1) enables the expected product to be isolated.

STEP 1:

(5R,5aR,8aS,9R)-5-{[(2S,6R,8R)-8-amino-2-methylhexahydropyrano[3,2-d][1,3]-dioxin-6-yl]oxy}-9-(4-hydroxy-3,5-dimethoxyphenyl)-5,8,8a,9-tetrahydrofurol3',4':6,7]naphtho[2,3-d][1,3]dioxol-6(5aH)-one The procedure is as in Example 4, using as substrate the product obtained in Step 1 above.

EXAMPLE 23

4-((5R,5aS,8aR,9R)-9-{[(4-fluoroanilino)carbonyl]oxy}-8-oxo-5,5a,6,8,8a,9-hexahydrofuro[3',4':6,7]naphtho[2,3-d][1,3]dioxol-5-yl)-2,6-dimethoxyphenyl 4-nitrophenyl carbonate 1.07 mmol of pyridine and then, dropwise, a solution of 0.59 mmol of the compound of Example 4 in 5 ml of dichloromethane, are added, under argon, to a solution of 0.83 mmol of para-nitrophenyl chloroformate in 20 ml of anhydrous dichloromethane. After stirring for 1 hour, the reaction mixture is hydrolysed by the addition of a saturated aqueous NaHCO$_3$ solution, and then the extracted organic phases are washed, neutralised, dried, filtered and concentrated under reduced pressure. Chromatography on silica gel (cyclohexane/ethyl acetate: 3/1) enables the expected product to be isolated.

EXAMPLE 24

4((5R,5aS,8aR,9R)-9-{[(4-fluoroanilino)carbonyl]oxy}-8-oxo-5,5a,6,8,8a,9-hexahydrofuro[3',4':6,7]naphtho[2,3-d][1,3]-dioxol-5-yl)-2,6-dimethoxyphenyl 4-piperidinyl-1-piperidinecarboxylate 0.87 mmol of triethylamine and 0.87 mmol of 4-piperidino-piperidine are added, under an argon atmosphere, to a solution of 0.56 mmol of the compound of Example 23 in 20 ml of anhydrous dichloromethane. After 2 hours, 20 ml of water are added to the reaction mixture. After extraction with dichloromethane, washing, drying, filtration, and concentration of the organic phases under reduced pressure, chromatography on silica gel (dichloromethane, methanol: 95/5) enables the expected product to be isolated.

PHARMACOLOGICAL STUDY OF THE COMPOUNDS OF THE INVENTION

EXAMPLE 25

In vitro Activity

Murine leukaemia L1210 and human colon carcinoma HT-29 were used in vitro. The cells are cultured in RPMI 1640 complete culture medium comprising 10% foetal calf serum, 2 mM glutamine, 50 units/ml of penicillin, 50 µg/ml of streptomycin and 10 mM Hepes, pH 7.4. The cells are distributed on microplates and are exposed to the cytotoxic compounds for four doubling periods, that is to say 48 hours (L1210) or 96 hours (HT-29). The number of viable cells is then quantified by a calorimetric assay, the Microculture Tetrazolium Assay (J. Carmichael et al., *Cancer Res.*; 47, 936–942, (1987)). The results are expressed as IC$_{50}$, the cytotoxic concentration that inhibits the proliferation of the treated cells by 50%.

In this test, the compound of Example 9 has an IC$_{50}$ of 88 nM.

EXAMPLE 26

Action on the Cell Cycle

L1210 cells are incubated for 21 hours at 37° C. in the presence of various concentrations of test compounds. The cells are then fixed using 70% ethanol (v/v), washed twice in PBS and incubated for 30 minutes at 20° C. in PBS that contains 100 µg/ml of RNAse and 50 µg/ml of propidium iodide. The results are expressed as a percentage of the cells that have accumulated in the G2+M phase after 21 hours, compared with the control (control: 20%). The compound of Example 9 induces a 75% accumulation of the cells in the G2+M phase after 21 hours at a concentration of 1 µM.

We claim:

1. A compound selected from those of formula (I):

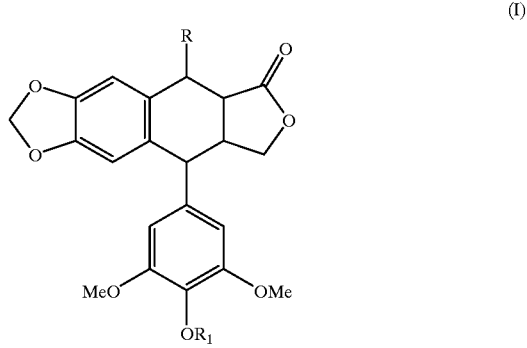

(I)

wherein:

R represents:

a group of formula (i):

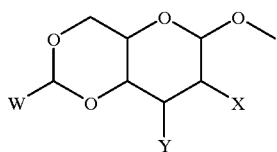

(i)

wherein:
X and Y, which may be identical or different, each represent a group selected from hydrogen, hydroxy, linear or branched ($C_1$–$C_6$)alkoxy, amino, linear or branched ($C_1$–$C_6$)alkylamino and di-($C_1$–$C_6$) alkylamino in which each alkyl moiety may be linear or branched, W represents hydrogen, linear or branched ($C_1$–$C_6$)alkyl, aryl or heteroaryl, or a group of formula (ii):

—A—G  (ii)

wherein:
A represents a single bond or a linear or branched ($C_1$–$C_6$) alkylene chain optionally substituted by one or more identical or different groups selected from halogen and hydroxy and optionally containing an unsaturation, G represents a group selected from hydrogen, cycloalkyl, heterocycloalkyl, aryl, heteroaryl, —$OR_2$, —O—$T_1$—$NR_3R_4$, —O—$T_1$—$NR_2$—$T'_1$—$NR_3R_4$, —$NR_3R_4$, —$NR_2$—$T_1$—$NR_3R_4$, —$NR_2$—$T_1$—$OR_5$, —$NR_2$—$T_1$—$CO_2R_6$, —$NR_2$—$T_1$—$C(O)R_6$, —$C(O)$—$NR_3R_4$, —$C(O)$—$NR_2$—$T_2$, —O—$C(O)$—$T_2$, —O—$C(S)$—$T_2$, —$NR_2$—$C(O)$—$T_2$, —$NR_2$—$C(S)$—$T_2$, —O—C(O)—O—$T_2$, —O—$C(O)$—$NR_2$—$T_2$, —O—$C(S)$—O—$T_2$, —O—$C(S)$—$NR_2$—$T_2$, —$NR_2$—$C(O)$—O—$T_2$, —$NR_2$—$C(O)$—$NR_6$—$T_2$, —$NR_2$—$C(S)$—O—$T_2$, —$NR_2$—$C(S)$—$NR_6$—$T_2$ and —$NR_2$—$SO_2$—$T_3$ wherein:
$R_2$ represents hydrogen, linear or branched ($C_1$–$C_6$) alkyl, aryl or aryl-($C_1$–$C_6$)alkyl in which the alkyl moiety may be linear or branched, $T_1$ and $T'_1$, which may be identical or different, each represents a linear or branched ($C_1$–$C_6$)alkylene chain, $R_3$ and $R_4$, which may be identical or different, each represent independently of the other:
hydrogen, linear or branched ($C_1$–$C_6$)alkyl (optionally substituted by one or more hydroxy), aryl, aryl-($C_1$–$C_6$)alkyl in which the alkyl moiety may be linear or branched, cycloalkyl, heteroaryl-($C_1$–$C_6$)alkyl in which the alkyl moiety may be linear or branched, heteroaryl, heterocycloalkyl or heterocycloalkyl-($C_1$–$C_6$)alkyl in which the alkyl moiety may be linear or branched, or form together with the nitrogen atom carrying them a saturated or unsaturated, 5- to 7-membered, monocyclic heterocycle optionally containing a second hetero atom selected from oxygen and nitrogen, the heterocycle being optionally substituted by one or more groups selected from halogen, hydroxy, linear or branched ($C_1$–$C_6$)alkyl and heterocyclic groups, $R_5$ represents linear or branched ($C_1$–$C_6$)alkyl, aryl or aryl-($C_1$–$C_6$)alkyl in which the alkyl moiety may be linear or branched, $R_6$ represents hydrogen, linear or branched ($C_1$–$C_6$) alkyl, aryl or aryl-($C_1$–$C_6$)alkyl in which the alkyl moiety may be linear or branched, $T_2$ represents a group selected from hydrogen, linear or branched ($C_1$–$C_6$)alkyl (optionally substituted by one or more halogen), aryl, aryl-($C_1$–$C_6$)alkyl in which the alkyl moiety may be linear or branched, cycloalkyl, cycloalkyl-($C_1$–$C_6$)alkyl in which the alkyl moiety may be linear or branched, heterocycloalkyl and heterocycloalkyl-($C_1$–$C_6$)alkyl in which the alkyl moiety may be linear or branched, or $T_2$ represents a linear or branched ($C_1$–$C_6$)alkylene chain, the chain being substituted by one or more identical or different groups selected from —$NR_3R_4$, —$OR_2$, —$CO_2R_6$, —$NR_2$—$C(O)R_6$, —$NR_2$—$CO_2R_6$, —$C(O)R_6$, —$C(O)NR_3R_4$, —$NR_2$—$T_1$—$NR_3R_4$, —$NR_2$—$T_1$—$OR_6$ and —O—$T_1$—$NR_3R_4$
wherein $R_2$, $R_3$, $R_4$, $R_6$ and $T_1$ are as defined hereinbefore, $T_3$ represents a group selected from linear or branched ($C_1$–$C_{20}$)alkyl (optionally substituted by one or more groups selected from halogen, —$OR_2$, —$NR_2R_6$, nitro, cyano and azide), aryl, aryl-($C_1$–$C_6$)alkyl in which the alkyl moiety may be linear or branched, cycloalkyl, cycloalkyl-($C_1$–$C_6$)alkyl in which the alkyl moiety may be linear or branched, heterocycloalkyl, heterocycloalkyl-($C_1$–$C_6$)alkyl in which the alkyl moiety may be linear or branched, heteroaryl and heteroaryl-($C_1$–$C_6$)alkyl in which the alkyl moiety may be linear or branched, $R_1$ represents a group selected from hydrogen, linear or branched ($C_1$–$C_6$)alkyl, aryl, aryl-($C_1$–$C_6$)alkyl in which the alkyl moiety may be linear or branched, heteroaryl, heteroaryl-($C_1$–$C_6$)alkyl in which the alkyl moiety may be linear or branched, linear or branched ($C_1$–$C_6$)alkylcarbonyl, arylcarbonyl, aryl-($C_1$–$C_6$) alkylcarbonyl in which the alkyl moiety may be linear or branched, heterocycloalkylcarbonyl, linear or branched ($C_1$–$C_6$)alkylsulphonyl, arylsulphonyl, aryl-($C_1$–$C_6$)alkylsulphonyl in which the alkyl moiety may be linear or branched, phosphono, linear or branched ($C_1$–$C_6$)alkoxycarbonyl, aryloxycarbonyl and aryl-($C_1$–$C_6$)alkoxycarbonyl in which the alkoxy moiety may be linear or branched, its isomers, and also addition salts thereof with a pharmaceutically acceptable acid or base, wherein:
aryl denotes phenyl, biphenyl, naphthyl, dihydronaphthyl, tetrahydronaphthyl, indenyl or indanyl, each of those groups optionally having one or more identical or different substituents selected from halogen, hydroxy, linear or branched ($C_1$–$C_6$)alkyl, linear or branched ($C_1$–$C_6$)alkoxy, cyano, nitro, amino, linear or branched ($C_1$–$C_6$)alkylamino, di-($C_1$–$C_6$)alkylamino in which each alkyl moiety may be linear or branched, linear or branched ($C_1$–$C_6$)alkylsulphonyl, linear or branched ($C_1$–$C_6$)alkylsulphonylamino, carboxy, linear or branched ($C_1$–$C_6$)alkoxycarbonyl, aryloxycarbonyl, aryl-($C_1$–$C_6$)alkoxycarbonyl in which the alkoxy moiety may be linear or branched, linear or branched ($C_1$–$C_6$)hydroxyalkyl, linear or branched ($C_1$–$C_6$) trihaloalkyl, methylenedioxy, ethylenedioxy, morpholinyl, piperidyl, piperazinyl, linear or branched ($C_1$–$C_6$)alkylcarbonyloxy and linear or branched ($C_1$–$C_6$)alkylcarbonyl, heteroaryl denotes an aromatic monocyclic group, an aromatic bicyclic group, or a bicyclic group in which one of the rings is aromatic and the other ring is partially hydrogenated, each of which groups has from 5 to 12 ring members and contains in the ring system one, two or three identical or different hetero atoms selected from oxygen, nitrogen and sulphur, it being possible for the said heteroaryl optionally to be substituted by the same substituents as those decribed in the case of the aryl group, cycloalkyl denotes a monocyclic or bicyclic group that is saturated or unsaturated, but not of aromatic character, that contains from 3 to 10 carbon atoms and is optionally substituted by one or more identical or different groups selected from halogen, linear or branched $(C_1-C_6)$alkyl, linear or branched $(C_1-C_6)$trihaloalkyl, hydroxy, linear or branched $(C_1-C_6)$hydroxyalkyl, amino, linear or branched $(C_1-C_6)$alkylamino, di-$(C_1-C_6)$-alkylamino in which each alkyl moiety may be linear or branched, piperidyl, piperazinyl and morpholinyl, heterocycloalkyl is to be understood as a cycloalkyl group as defined above containing one or two identical or different hetero atoms selected from oxygen, nitrogen and sulphur, the said heterocycloalkyl being optionally substituted by one or more substituents such as those described in the case of the cycloalkyl, with the proviso that $R_1$ does not represent methyl when R represents a group —A—G in which A represents a single bond and G represents hydrogen.

2. Compound of claim 1, wherein $R_1$ represents a group selected from hydrogen, linear or branched $(C_1-C_6)$alkyl, linear or branched $(C_1-C_6)$alkoxycarbonyl, aryloxycarbonyl and aryl-$(C_1-C_6)$alkoxycarbonyl in which the alkoxy moiety may be linear or branched.

3. Compound of claim 1, wherein $R_1$ represents hydrogen.

4. Compound of claim 1, wherein R represents a group of formula (i) as defined for formula (I), wherein:

X represents amino, linear or branched $(C_1-C_6)$ alkylamino or di-$(C_1-C_6)$alkylamino in which each alkyl moiety may be linear or branched, and Y represents hydroxy; or X and Y are identical and each represents hydroxy; or X represents hydrogen and Y represents amino, linear or branched $(C_1-C_6)$ alkylamino or di-$(C_1-C_6)$alkylamino in which each alkyl moiety may be linear or branched and W represents methyl or 2-thienyl.

5. Compound of claim 1, wherein R represents a group of formula (i) such as:

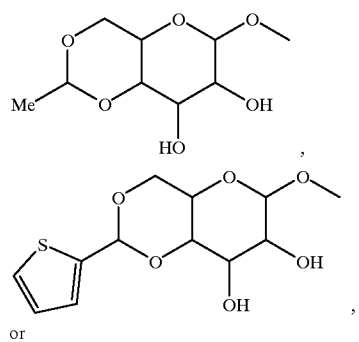

or

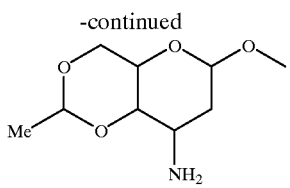

6. Compound of claim 1, wherein R represents a group of formula (ii) as defined for formula (I) wherein:

A represents a single bond and

G represents a group selected from O—$T_1$—$NR_3R_4$, —O—$T_1$—$NR_2$—$T'_1$—$NR_3R_4$, —$NR_2$—$T_1$—$NR_3R_4$, —$NR_3R_4$, —$NR_2$—T—$OR_5$, —O—C(O)—$NR_2$—$T_2$ and —$NR_2$—$SO_2$—$T_3$ in which $T_1$, $T'_1$, $T_2$, $T_3$, $R_2$, $R_3$, $R_4$ et $R_5$ are as defined for formula (I).

7. Compound of either claim 1, wherein R represents a group of formula (ii) as defined for formula (I), wherein:

A represents a single bond and

G represents a group —O—C(O)—$NR_2$—$T_2$ wherein $R_2$ and $T_2$ are as defined for formula (I) and, advantageously, $R_2$ represents hydrogen or linear or branched $(C_1-C_6)$alkyl and $T_2$ represents an optionally substituted aryl group or a linear or branched $(C_1-C_6)$ alkylene chain substituted by —$NR_3R_4$ wherein $R_3$ and $R_4$ are as defined for formula (I).

8. Compound of either claim 1, wherein R represents a group of formula (ii) as defined for formula (I) wherein:

A represents a single bond and

G represents —$NR_2$—$SO_2$—$T_3$ wherein $R_2$ and $T_3$ are as defined for formula (I) and, advantageously, $R_2$ represents hydrogen or linear or branched $(C_1-C_6)$alkyl and $T_3$ represents linear or branched $(C_1-C_6)$alkyl, aryl or heteroaryl.

9. Compound of claim 1 selected from the group consisting of:

9-(4-hydroxy-3,5-dimethoxyphenyl)-6-oxo-5,5a,6,8,8a, 9-hexahydrofuro[3',4':6,7]naphtho[2,3-d][1,3]dioxol-5-yl 4-fluorophenylcarbamate, 9-(4-hydroxy-3,5-dimethoxyphenyl)-6-oxo-5,5a,6,8,8a, 9-hexahydrofuro[3',4':6,7]naphtho[2,3-d][1,3]dioxol-5-yl 2-(dimethylamino)ethyl(methyl)carbamate, 9-(4-hydroxy-3,5-dimethoxyphenyl)-6-oxo-5,5a,6,8,8a, 9-hexahydrofuro[3',4':6,7]naphtho[2,3-d][1,3]-dioxol-5-yl 2-(dimethylamino)ethylcarbamate, 9-(4-hydroxy-3,5-dimethoxyphenyl)-6-oxo-5,5a,6,8,8a, 9-hexahydrofuro[3',4':6,7]naphtho[2,3-d][1,3]dioxol-5-yl 3-(dimethylamino)propyl(methyl)carbamate, and 9-(4-hydroxy-3,5-dimethoxyphenyl)-6-oxo-5,5a,6,8, 8a,9-hexahydrofuro[3',4':6,7]naphtho[2,3-d][1,3] dioxol-5-yl 3-(dimethylamino)propylcarbamate, and their isomers, and also addition salts thereof with a pharmaceutically acceptable acid or base.

10. Compound of claim 1 selected from the group consisting of:

(5R,5aR,8aS,9R)-9-(4-hydroxy-3,5-dimethoxyphenyl)-6-oxo-5,5a,6,8,8a,9-hexahydrofuro[3',4':6,7]naphtho[2, 3-d][1,3]dioxol-5-yl 4-fluorophenylcarbamate, (5R,5aS,8aR,9R)-9-(4-hydroxy-3,5-dimethoxyphenyl)-6-oxo-5,5a,6,8,8a,9-hexahydrofuro [3',4':6,7]naphtho [2,3-d][1,3]dioxol-5-yl 2-(dimethylamino)ethyl (methyl)carbamate, (5R,5aR,8aS,9R)-9-(4-hydroxy-3,5-dimethoxyphenyl)-6-oxo-5,5a,6,8,8a,9-hexahydrofuro[3',4':6,7]naphtho[2, 3-d][1,3]-dioxol-5-yl 2-(dimethylamino)
ethylcarbamate, (5R,5aR,8aS,9R)-9-(4-hydroxy-3,5-dimethoxyphenyl)-6-oxo-5,5a,6,8,8a,9-hexahydrofuro[3',4':6,7]naphtho[2,3-d][1,3]dioxol-5-yl 3-(dimethylamino)propyl(methyl)carbamate and (5R,5aS,8aR,9R)-9-(4-hydroxy-3,5-dimethoxyphenyl)-6-oxo-5,5a,6,8,8a,9-hexahfuro[3',4':6,7]naphtho[2,3-d][1,3]dioxol-5-yl 3-(dimethylamino)propylcarbamate.

11. Compounds of formulae

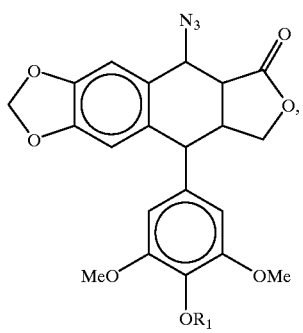

(XIa)

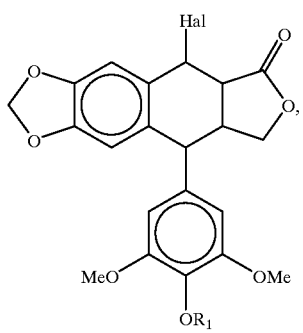

(XIV)

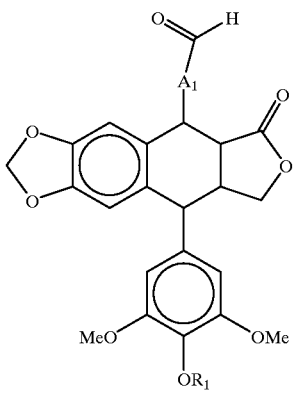

(XVII)

and for use as synthesis intermediates for the preparation of the compounds of formula (I).

12. A method for treating a living animal body afflicted with cancer comprising the step of administering to the living body an amount of a compound of claim 1, which is effective for alleviation of said cancer.

13. A pharmaceutical composition useful in treating cancer comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO.    : 6,281,198 B1  
DATED         : August 28, 2001  
INVENTOR(S)   : Claude Monneret et al.

Page 1 of 1

It is certified that error appears in the above-identified patent and that said Letters Patent is hereby corrected as shown below:

Title page,  
Title, "TETRAHYDROFURO-[3',4':6,7]" should read  
-- TETRAHYDROFURO [3',4':6,7] --.

ABSTRACT,  
Line 30, "-O-C(O)T$_2$," should read -- -O-C(O)-T$_2$, --; and  
Line 34, "-NR$_2$-C(O)-NR-T$_2$," should read -- -NR$_2$-C(O)-NR$_6$-T$_2$, --.

Column 27,  
Line 45, "represents hydroxy" should read -- represent hydroxy --.

Column 28,  
Line 15, "-NR$_2$-T-OR$_5$," should read -- NR$_2$-T$_1$-OR$_5$, --.

Signed and Sealed this

Thirtieth Day of April, 2002

*Attest:*

*Attesting Officer*

JAMES E. ROGAN  
*Director of the United States Patent and Trademark Office*